US00PP24996P3

(12) United States Plant Patent

Skotak, Jr.

(10) Patent No.: US PP24,996 P3

(45) Date of Patent: Oct. 21, 2014

(54) *GUZMANIA* PLANT NAMED 'DURAREV'

(50) Latin Name: *Guzmania lingulata×wittmackii*
Varietal Denomination: DURAREV

(76) Inventor: Chester Skotak, Jr., Alajuela (CR)

( * ) Notice: Subject to any disclaimer, the term of this patent is extended or adjusted under 35 U.S.C. 154(b) by 251 days.

(21) Appl. No.: 13/507,704

(22) Filed: Jul. 20, 2012

(65) Prior Publication Data

US 2014/0026271 P1 Jan. 23, 2014

(51) Int. Cl.
*A01H 5/00* (2006.01)

(52) U.S. Cl.
USPC ..... Plt./371

(58) Field of Classification Search
USPC ..... Plt./371
See application file for complete search history.

*Primary Examiner* — Kent L Bell
(74) *Attorney, Agent, or Firm* — Cassandra Bright

(57) ABSTRACT

A new and distinct *Guzmania* cultivar named 'DURAREV' is disclosed, characterized by red inflorescence and compact plant shape. The new variety is a *Guzmania*, typically produced as an indoor ornamental plant.

1 Drawing Sheet

Latin name of the genus and species: *Guzmania lingulata×wittmackii.*

Variety denomination: 'DURAREV'.

BACKGROUND OF THE INVENTION

The new cultivar is a product of a planned breeding program. The new variety originated from a cross pollination of an unnamed, unpatented *Guzmania lingulata×wittmackii* seed parent and the pollen parent, an unnamed, unpatented variety of *Guzmania lingulata*. The crossing was made during 2005.

The new variety was discovered by the inventor, Chester Skotak Jr., a citizen of Costa Rica, in September 2008 in a group of seedlings resulting from the crossing. The new cultivar was found in a commercial greenhouse in Alajuela, Costa Rica.

Asexual reproduction of the new cultivar 'DURAREV' was first performed at a commercial laboratory in Belgium by tissue culture during February of 2011. Subsequent propagation by tissue culture has shown that the unique features of this cultivar are stable and reproduced true to type.

SUMMARY OF THE INVENTION

The cultivar 'DURAREV' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DURAREV.' These characteristics in combination distinguish 'DURAREV' as a new and distinct *Guzmania* cultivar:

1. Red inflorescence.
2. Compact plant shape.

PARENT COMPARISON

Plants of the new cultivar 'DURAREV' are similar to the unpatented seed parent in most horticultural characteristics. The new variety however differs in the following characteristic:

1. 'DURAREV' has a red inflorescence whereas the seed parent has a yellow inflorescence.

Plants of the new cultivar 'DURAREV' are similar to the pollen parent in most horticultural characteristics. The new variety however differs in the following characteristic:

1. 'DURAREV' is shorter than the pollen parent.

COMMERCIAL COMPARISON

'DURAREV' can be compared to the unpatented commercial variety of *Guzmania* known as 'Class'. Plants of *Guzmania* 'Class' are similar to plants of 'DURAREV' in most horticultural characteristics. However 'DURAREV' differs from 'Class' in the following characteristics:

1. 'DURAREV' is a smaller plant than 'Class'
2. 'DURAREV' produces a flower that is more red in color than the orange-red color of 'Class'.
3. Plants of 'DURAREV' produce leaves with more anthocyanin flushing than those of 'Class'.

BRIEF DESCRIPTION OF THE PHOTOGRAPH

The accompanying photograph in FIG. 1 illustrates in full color a typical plant of 'DURAREV' grown in a greenhouse in Altha, Fla. This plant is approximately 16 months old, shown in an 18 cm. pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'DURAREV' plants grown in a climate controlled greenhouse in Evergem, Belgium. Temperatures ranged from 18° C. to 22° C. at night to 20° C. to 28° C. during the day. No artificial light, photoperiodic or chemical treatments were given to the plants. Measurements and numerical values represent averages of typical plant types.

Botanical classification: *Guzmania lingulata×wittmackii* 'DURAREV'.

PROPAGATION

Type of propagation typically used: Tissue culture.

Time to initiate roots: About 15 days at approximately 20° C.

Time to produce a rooted cutting/liner: About 180 days at approximately 22° C.

Root description: Moderately dense, moderately branched, fine, fibrous, not fleshy, colored near RHS Brown 201A.

PLANT

Growth habit: Upright, monopodial.

Height: Average: 27.5 cm.

Plant spread: Average: 40.0 cm.

Normal pot size: 10.5 cm (circular).

Growth rate: Moderate.

Branching characteristics: Monopodial, leaves form a basal rosette, inflorescence grows from the center of the rosette. No stem present.

Number of leaves per scape: Average: 37.

FOLIAGE

Leaf:

*Arrangement*.—Rosulate; leaves (average: 37) placed in a basal rosette.

*Average length*.—Approximately 22.4 cm.

*Average width*.—Approximately 3.6 cm, lowest leaves narrower, average: 2.9 cm.

*Shape of blade*.—Ligulate.

*Aspect*.—Arching downward.

*Apex*.—Apiculate, curved downward.

*Base*.—Sheathing. Sheath length: Average 3.2 cm. Sheath width: Average 6.3 cm. Sheath color: Yellow-green, near RHS 145C.

*Margin*.—Entire.

*Texture of top surface*.—Smooth, very glossy.

*Texture of bottom surface*.—Smooth, very glossy.

*Color*.—Young foliage upper side: Yellow-green; near RHS 146C, top and margins greyed-purple, near RHS 187B and 187C. Young foliage under side: Greyed-red, near RHS 182A, upper half greyed-purple 183B. Mature foliage upper side: Green to yellow-green; in between RHS 137A and 146A, top slightly tinged greyed-purple, near RHS 183A, base green; 143C with a greyed-purple basal spot, near RHS 187C. Mature foliage under side: Green to yellow-green; in between RHS 138A and 147B, base yellow-green; 146C with a greyed-purple basal spot, near RHS 187C.

*Venation*.—Type: Parallel. Venation coloration: Green to yellow-green; in between RHS 137A and 146A.

Petiole: No petioles present, leaves sheathing.

INFLORESCENCE

General description:

*Inflorescence height, excluding scape*.—Approximately 7.2 cm.

*Inflorescence width*.—Approximately 14.0 cm.

Scape:

*Length*.—Approximately 21.0 cm.

*Width*.—Approximately 1.0 cm.

*Aspect*.—Approximately 90° angle to rosette (near vertical).

*Strength*.—Very strong.

*Color*.—Yellow-green, near RHS 150D.

Bracts:

*Scape/lowermost bracts*.—Shape: Ligulate. Length: Approximately 12.3 cm (excluding sheath). Width: Approximately 2.9 cm. Quantity: Average 10. Tip: Apiculate. Base: Sheathing. Sheath length: Approximately 1.8 cm. Sheath width: Approximately 3.2 cm. Sheath color: Yellow-green, near RHS 145C. Margin: Color Upperside: Upper half yellow-green to brown, a color in between RHS 147A and N200A, closest to N200A, lower half greyed-red, near 180A, red towards the base, near RHS 42C. Color Underside: Upper half yellow-green, near RHS 147A, lower half greyed-purple, near 184A, red towards the base, near RHS 42B.

*Terminal bracts*.—Shape: Short ligulate. Length: Approximately 5.0 cm (excluding sheath). Width: Approximately 3.4 cm. Quantity: Average 24. Tip: Acute. Base: Sheathing. Sheath length: Approximately 1.2 cm. Sheath width: Approximately 3.6 cm. Sheath color: Yellow-green, near RHS 150D. Margin: Entire. Coloration Terminal Bracts: Upperside: Red, near RHS 42A, top darker, near RHS 46B. Underside: Near RHS Red 42A.

OTHER CHARACTERISTICS

Disease resistance: Neiether resistance nor susceptibility to the normal diseases and pests of *Guzmania* has been observed.

Drought tolerance and cold tolerance: Observed to tolerate temperatures to 40° C. without any negative effects. Temperature tolerance above this range has not been observed. Tolerance of cold temperatures has not been observed.

Fruit/seed production: Not observed to date.

What is claimed is:

1. A new and distinct cultivar of *Guzmania* plant named 'DURAREV' as herein illustrated and described.

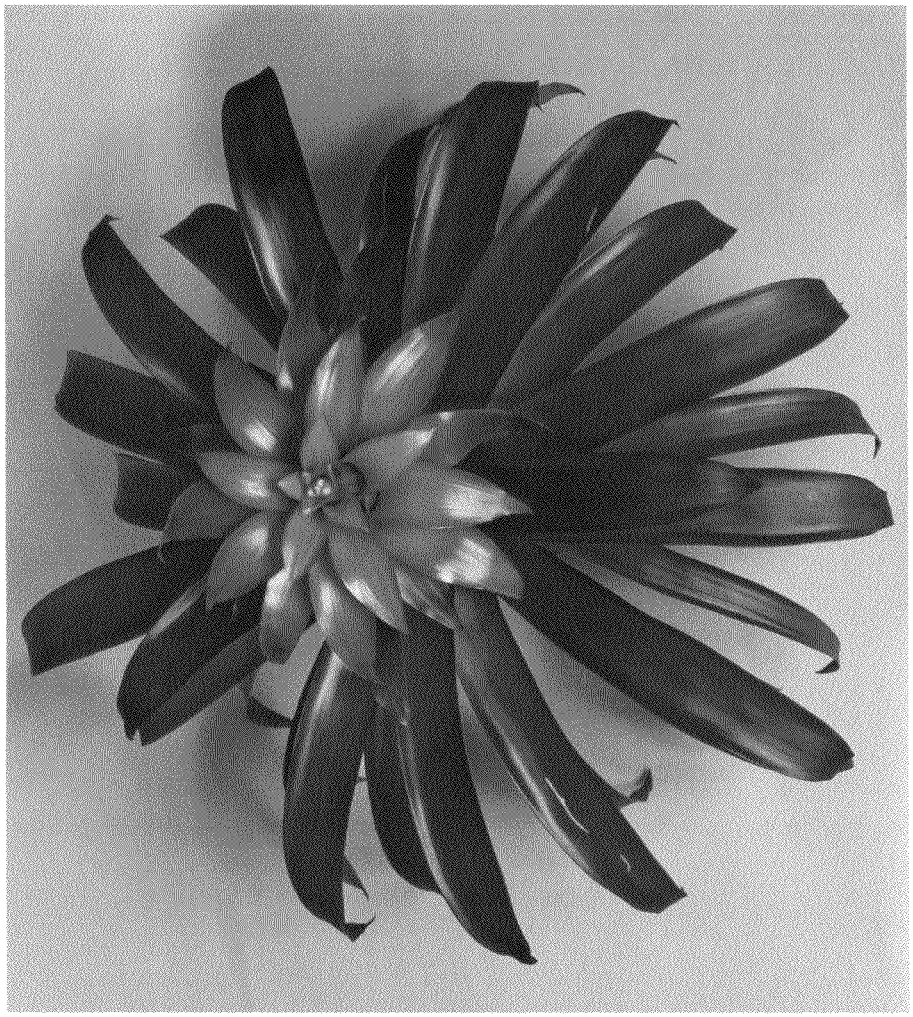

* * * * *